United States Patent [19]

Cavero et al.

[11] Patent Number: 4,520,030
[45] Date of Patent: May 28, 1985

[54] ANTI-ULCER AGENTS

[75] Inventors: Icilio Cavero, Creteil; Salomon Langer, Paris, both of France

[73] Assignee: Synthelabo, Paris, France

[21] Appl. No.: 560,250

[22] Filed: Dec. 12, 1983

[51] Int. Cl.³ .......................................... A61K 31/165
[52] U.S. Cl. .................................... 514/629; 514/926
[58] Field of Search ......................................... 424/324

[56] References Cited

PUBLICATIONS

*Chemical Abstracts*, vol. 99, (1983), 53413n.

*Primary Examiner*—Frederick E. Waddell
*Attorney, Agent, or Firm*—Wegner & Bretschneider

[57] ABSTRACT

2-Dipropylamino-5 or -7-formylamino-6-hydroxy-1,2,3,4-tetrahydronaphthalene and their pharmaceutically acceptable salts are useful as anti-ulcer agents.

4 Claims, No Drawings

ANTI-ULCER AGENTS

A method of treating a patient having gastric or duodenal ulcer or gastric hypersecretion is provided which comprises treating said patient with a compound of the formula

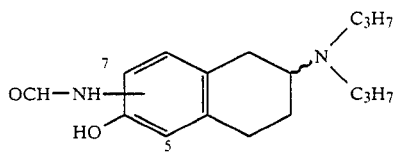

wherein the formylamino group is in the 5— or 7—position, or a pharmaceutically acceptable salt thereof.

These compounds can be prepared in accordance with the methods described in European patent application No. 74 903.

EXAMPLE 1

2-Dipropylamino-5-formylamino-6-hydroxy-1,2,3,4-tetrahydronaphthalene hydrobromide.

(a) 2-Dipropylamino-6-methoxy-1,2,3,4-tetrahydronaphthalene.

20 g of 6-methoxytetrahydronaphthalen-2-one, 20 ml of dipropylamine and 200 mg of para-toluenesulphonic acid are introduced into 300 ml of benzene under a nitrogen atmosphere. The mixture, which has become black, is then heated under reflux for 12 hours, the water of condensation being removed by azeotropic distillation. The solution is then concentrated to a volume of about 100 ml. For the hydrogenation, 150 ml of ethanol and 300 mg of $PtO_2$ are added thereto and hydrogenation is carried out, under a pressure of about 0.3 MPa, until the absorption has stopped.

After removal of the catalyst, the solvents are driven off under reduced pressure and the residual black oil is taken up in toluene and extracted with N hydrochloric acid. The hydrochloric acid solution is then neutralised with an alkali and extracted with toluene, the organic phase is dried and filtered on 200 g of neutral alumina, and elution is completed by means of methylene chloride. Concentration gives a virtually colourless oil.

(b) 2-Dipropylamino-6-methoxy-5(and 7)-nitro-1,2,3,4-tetrahydronaphthalene.

21 g of 2-dipropylamino-6-methoxy-1,2,3,4-tetrahydronaphthalene are added to 60 ml of trifluoroacetic acid, with simultaneous cooling of the mixture. 7 ml of nitric acid (d=2.42) are then added dropwise, the temperature being kept at about 0° C. The mixture is stirred for a further 10 minutes, the whole is poured into water and the insoluble material is extracted with methylene chloride; the organic phase is shaken with a solution of potassium carbonate and washed with water.

After drying and evaporation, the brown gum obtained is subjected to chromatography on a column of neutral alumina (800 g), elution being carried out with toluene. The less polar compound is the isomer nitrated in the 5-position. 9 g of each of the isomers are obtained. The compound nitrated in the 5-position melts at 198°–220° C. and the compound nitrated in the 7-position melts at 158°–160° C. (in the form of the hydrochlorides).

(c) 2-Dipropylamino-6-hydroxy-5-nitro-1,2,3,4-tetrahydronaphthalene hydrobromide.

9 g of 2-dipropylamino-6-methoxy-5-nitro-1,2,3,4-tetrahydronaphthalene are introduced into 100 ml of 48% hydrobromic acid and the mixture is heated under reflux for 2 hours. The acid is then driven off under reduced pressure and the residue is taken up three times in water, the water being evaporated off each time in order to remove any trace of acid. When recrystallised from water, the solid obtained forms a monohydrate which melts at 236° C. (with decomposition).

(d) 2-Dipropylamino-5-amino-6-hydroxy-1,2,3,4-tetrahydronaphthalene hydrobromide.

7 g of 2-dipropylamino-6-hydroxy-5-nitro-1,2,3,4-tetrahydronaphthalene hydrobromide are suspended in 250 ml of ethanol and hydrogenation is carried out at ambient temperature, in the presence of 1 g of 5% palladium-on-charcoal, under a pressure of about 0.3 MPa. The solvent is then evaporated off and the residue is triturated in diethyl ether. The product obtained melts at 215°–218° C. (with decomposition).

(e) 2-Dipropylamino-5-formylamino-6-hydroxy-1,2,3,4-tetrahydronaphthalene hydrobromide.

0.42 ml of acetic anhydride is added all at once to 2 ml of 98% formic acid, kept at 0° C., and the mixture is left at 0° C. for 15 minutes. Then, still using an ice-bath, 1.34 g of 2-dipropylamino-5-amino-6-hydroxy-1,2,3,4-tetrahydronaphthalene hydrobromide are introduced therein with a spatula and the whole is stirred for one hour at 0° C. After 50 ml of diethyl ether have been added and the solid has been filtered off, the latter is recrystallised from a 50/50 methanol/ethyl acetate mixture. This gives 1 g of the final product melting at 213° C. (with decomposition).

EXAMPLE 2

2-Dipropylamino-7-formylamino-6-hydroxy-1,2,3,4-tetrahydronaphthalene hydrobromide.

(a) 2-Dipropylamino-7-amino-6-methoxy-1,2,3,4-tetrahydronaphthalene.

9 g of the 2-dipropylamino-6-methoxy-7-nitro-1,2,3,4-tetrahydronaphthalene obtained in accordance with Example 1(b) are introduced into 200 ml of ethanol, together with 1 g of Raney nickel. At ambient temperature, hydrogenation is carried out under pressure until the absorption has stopped. After evaporation of the solvent, an oil remains which is shown to oxidise fairly readily in air.

(b) 2-Dipropylamino-7-amino-6-hydroxy-1,2,3,4-tetrahydronaphthalene dihydrobromide.

The product obtained above is introduced in 100 ml of 48% hydrobromic acid, the mixture is heated under reflux for 10 hours and the acid is then driven off under reduced pressure and subsequently removed completely by distillation with a toluene/ethanol mixture in a rotary evaporator. After recrystallisation from isopropyl alcohol, the dihydrobromide melts at 250° C. (with decomposition).

(c) 2-Dipropylamino-7-amino-6-hydroxy-1,2,3,4-tetrahydronaphthalene monohydrobromide.

A solution of 5 ml of Amberlite LA2 resin in 50 ml of petroleum ether is added to a solution of 3 g of the dihydrobromide obtained in (b) above in 50 ml of water. The mixture is shaken for 15 minutes at ambient temperature and the aqueous phase is separated off and evaporated to dryness in order to isolate the crude monhydrobromide, in an amorphous and coloured form, which is used as such for the formylation.

(d) 2-Dipropylamino-7-formylamino-6-hydroxy-1,2,3,4-tetrahydronaphthalene hydrobromide.

0.7 ml of acetic anhydride is added to 3 ml of 98% formic acid, kept at 0° C., and the whole is left for 15 minutes at 0° C. 2.2 g of 2-dipropylamino-7-amino-6-hydroxy-1,2,3,4-tetrahydronaphthalene hydrobromide are then added thereto and the mixture is then stirred for one hour at 0° C. After 50 ml of diethyl ether have been added and the solid has been filtered off, the latter is recrystallised from a 50/50 methanol/ethyl acetate mixture. This gives 1 g of the final product melting at 213° C. (with decomposition).

The compounds were tested for their action against stress ulcer and ulcer induced by phenylbutazone.

STRESS ULCER

The test is carried out according to the method of E. D. Senay and R. J. Levine (Proc. Soc. Exp. Biol, 1967, 124, 1221-1223) and R. J. Levine (A method for the rapid production of stress ulcers in rats. Peptic ulcers. Edited by C. J. Pfeifer, 92-97), on female Wistar rats weighing 180-210 g, fasting for 20 hours and distributed in randomized blocks.

The animals are confined in cylindrical boxes of 20 cm in length and 5 cm in diameter, placed in a cold room at 2°-4° C. The anti-ulcers agents (compound of Example 1 or 2, or Diazepam for comparison) are administered per os immediately before the confinement, whereas the control animals are administered with a placebo.

The animals are sacrificed 2 hours later by inhalation of chloroform. Their stomachs are examined and the degree of ulceration noted.

PHENYLBUTAZONE INDUCED ULCER

The test is performed on female Wistar rats weighing 180-210 g, fasting for 20 hours and distributed in randomized blocks. Ulcers are induced by oral administration of phenylbutazone dissolved in sodium hydroxide (1 mole for 1 mole) at a dose of 200 mg/kg.

The anti-ulcer agents (compound of Example 1 or 2, or Cimetidine for comparison) are administered per os 30 minutes prior to the administration of phenylbutazone, with the control animals receiving only a placebo.

The animals are sacrificed 2 hours after administration of the ulcer inducing agent, by inhalation of chloroform. Their stomachs are examined and the degree of ulceration noted.

EXPRESSION OF RESULTS

In both the tests the degree of ulceration is noted using a scale of 0 to 3 after a macroscopic examination of the gastric mucous wall: 0 for a normal mucous wall; 0.5 for one haemorrhagic point; 1 for one small ulcer or a few haemorrhagic points; 1.5 for two small ulcers; 2 for three small ulcers or one large ulcer; 2.5 for more than three small ulcers or two large ulcers; 3 for a lot of small ulcers or more than two large ulcers.

The mean average ± confidence interval is calculated according to the Kruskal-Wallis test.

The ulceration index is the product of the degree of ulceration multiplied by the percentage of animals exhibiting ulcers; its value takes account of both the degree of ulceration and the number of affected animals.

RESULTS

The following tables show the results obtained.

TABLE I

| | | | Stress ulcer | | |
|---|---|---|---|---|---|
| Compound | Dose (mg/kg) | Degree of ulceration (A) | % Animals exhibiting ulcer (B) | Ulceration index (A × B) | % Decrease in ulceration index |
| Placebo | — | 2.45 ± 0.47 | 100 | 245 | — |
| Diazepam | 10.0 | 0.65 ± 0.46** | 60 | 39 | 84 |
| Example 1 | 0.3 | 2.18 ± 0.45 | 100 | 218 | 11 |
|  | 1.0 | 1.38 ± 0.72* | 80 | 110 | 55 |
|  | 3.0 | 1.28 ± 0.60** | 70 | 90 | 63 |
| Placebo | — | 2.55 ± 0.31 | 100 | 255 | — |
| Diazepam | 10. | 0.43 ± 0.56** | 40 | 17 | 93 |
| Example 2 | 0.3 | 2.33 ± 0.60 | 90 | 210 | 18 |
|  | 1.0 | 1.20 ± 0.74* | 80 | 96 | 62 |
|  | 3.0 | 0.48 ± 0.53** | 40 | 19 | 93 |

*$p < 0.05$
**$p < 0.01$ } Kruskall-Wallis test.

TABLE II

| | | | Phenylbutazone induced ulcer | | |
|---|---|---|---|---|---|
| Compound | Dose (mg/kg) | Degree of ulceration (A) | % Animals exhibiting ulcer (B) | Ulceration index (A × B) | % Decrease in ulceration index |
| Placebo | — | 2.60 ± 0.55 | 100 | 260 | — |
| Cimetidine | 10.0 | 1.05 ± 0.87* | 50 | 53 | 80 |
| Example 1 | 0.3 | 2.38 ± 0.59 | 100 | 238 | 8 |
|  | 1.0 | 1.43 ± 0.93 | 80 | 114 | 56 |
|  | 3.0 | 1.00 ± 0.90* | 50 | 50 | 81 |
| Placebo | — | 2.89 ± 0.17 | 100 | 289 | — |
| Cimetidine | 10.0 | 0.61 ± 0.68* | 33 | 20 | 93 |
| Example 2 | 0.3 | 2.67 ± 0.40 | 100 | 267 | 8 |
|  | 1.0 | 1.28 ± 1.07* | 56 | 72 | 75 |
|  | 3.0 | 0.00 ± 0.00** | 0 | 0 | 100 |

*$p < 0.05$ } Kruskall-Wallis test.

TABLE II-continued

| | | | % Animals | | |
| | Dose | Degree of | exhibiting | Ulceration | % Decrease in |
| Compound | (mg/kg) | ulceration (A) | ulcer (B) | index (A × B) | ulceration index |

**p < 0.01

The above tests show that the compounds administered according to the invention reduce the gravity of gastric ulcers.

Therefore they can be administered to the human, in form of the free base or of a pharmaceutically acceptable acid addition salt thereof for the treatment of gastric or duodenal ulcer or gastric hypersecretion.

The compounds can be administered orally or parenterally, in the form of pharmaceutical compositions comprising the active substance together with usual excipients, e.g. tablets, lozenges, capsules, gelules, coated pills, drinkable or injectable solutions or suspensions.

The unit administration dose can range from 0.5 to 5 mg of active compound, so as to permit a daily dosage ranging from 1 to 20 mg.

We claim:

1. A method of treating gastric or duodenal ulcer or gastric hypersecretion in a patient, which comprises orally or parenterally administering to said patient a compound of the formula

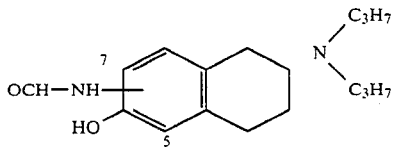

wherein the formylamino group is in the 5— or —7—position, or a pharmaceutically acceptable salt thereof, in an amount effective to treat gastric or duodenal ulcer or gastric hypersecretion.

2. A method according to claim 1, wherein said compound is 2-dipropylamino-5-formylamino-6-hydroxy-1,2,3,4-tetrahydronaphthalene or a pharmaceutically acceptable salt thereof.

3. A method according to claim 1, wherein said compound is 2-dipropylamino-7-formylamino-6-hydroxy-1,2,3,4-tetrahydronaphthalene or a pharmaceutically acceptable salt thereof.

4. A method according to claim 1, which comprises administering said compound at a daily dosage of 1 to 20 mg.

* * * * *